United States Patent [19]

Tolman et al.

[11] 4,277,603
[45] Jul. 7, 1981

[54] PREPARATION OF 5-DEAZARIBOFLAVINS

[75] Inventors: Richard L. Tolman, Warren; Wallace T. Ashton, Clark; Ronald D. Brown, Cranford, all of N.J.

[73] Assignee: Merck & Co., Inc., Rahway, N.J.

[21] Appl. No.: 19,986

[22] Filed: Mar. 12, 1979

Related U.S. Application Data

[63] Continuation-in-part of Ser. No. 960,341, Nov. 13, 1978, abandoned, which is a continuation-in-part of Ser. No. 894,299, Apr. 7, 1978, abandoned, which is a continuation of Ser. No. 753,664, Dec. 22, 1976, abandoned.

[51] Int. Cl.³ .................................. C07D 471/04
[52] U.S. Cl. ............................ 544/250; 544/310; 544/311; 260/340.9 R; 424/251
[58] Field of Search ................................ 544/250

[56] References Cited

PUBLICATIONS

Yoneda, et al., "J. C. S., Chem. Comm.," 1976, pp. 203–204.
O'Brien, et al., "Chem. Industry", 1967, pp. 2024–2045.
O'Brien, et al., "J. Heterocyclic Chem.," vol. 17, 1970, pp. 99–105.
Yoneda, et al., "J. Chem. Soc.," Perkin. Trans. I, No. 16, 1976, pp. 1804–1808.
Janda, et al., "Agnew Chem.," Int. Ed. (Engl.), vol. 15, 1976, pp. 443–444.

*Primary Examiner*—Anton H. Sutto
*Assistant Examiner*—James H. Turnipseed
*Attorney, Agent, or Firm*—David L. Rose; Harry E. Westlake

[57] ABSTRACT

This invention relates generally to a novel process for preparing 5-deazariboflavins by the cyclization of the corresponding 6-(N-substituted arylamino)uracils with trialkylorthoformate in the presence of a strong acid catalyst. An improved process for preparing the uracil intermediate is also disclosed. More particularly, it is concerned with the process for preparing 5-deazariboflavin by cyclizing 6-[3,4-dimethyl-N-(D-ribityl-)anilino[uracil with trialkylorthoformate in the presence of a strong acid catalyst and hydrolyzing the resulting alkoxymethylene derivative. The corresponding uracil intermediate is prepared by reacting 6-chlorouracil with N-D-ribityl-3,4-xylidine.

5-Deazariboflavins having the general Formula (I) herein below:

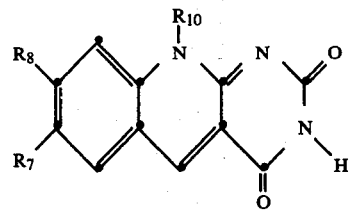

wherein $R_7$ is hydrogen or methyl, $R_8$ is methyl, hydroxy or acyloxy and $R_{10}$ is a ribityl group and the corresponding acyl and alkoxymethylene derivatives are useful as riboflavin antagonists with particular utility for the chemotherapy of coccidiosis in chickens or as intermediates for the preparation of said antagonists. The bis(alkoxymethylene) derivatives described herein are useful as prodrug forms of 5-deazariboflavins.

When used for the treatment of coccidiosis, such compounds are administered to the animals by way of the feed and are effective in preventing coccidiosis when administered at levels of from about 0.0005% to about 0.05% by weight of the total feed consumed, the amount required for optimum prevention or control of the disease varying with the particular compound employed.

20 Claims, No Drawings

PREPARATION OF 5-DEAZARIBOFLAVINS

CROSS REFERENCE TO RELATED CASES

This is a continuation-in-part of application Ser. No. 960,341, filed Nov. 13, 1978, now abandoned which is a continuation-in-part of application Ser. No. 894,299, filed Apr. 7, 1978, now abandoned which is a continuation of copending application Ser. No. 753,664, filed Dec. 22, 1976, now abandoned.

BACKGROUND OF THE INVENTION

A method for preparing 5-deazariboflavins has been described in D. E. O'Brien, L. T. Weinstock and C. C. Cheng, *Chem. Ind.*, 2044 (1967) and *J. Heterocycl. Chem.*, 7, 99 (1970). According to the numbering system adopted by these two references, 5-deazariboflavin is described as "10-deazariboflavin". The process described by O'Brien et al., based on the condensation of anthranilaldehydes with barbituric acid, entails a large number of steps and results in relatively low overall yields and is consequently cumbersome for large scale preparations.

The synthesis of 5-deazariboflavins from 6-(N-alkylanilino)uracils has been described by F. Yoneda and Y. Sakuma, J.C.S. Chem. Comm., 203 (1976). Yoneda et al. obtain 5-deazariboflavin analogs by the treatment of the corresponding 6-(N-alkylanilino)uracils with a mixture of phosphorous oxychloride or ethyl chloroformate and dimethylformamide. The process had not been extended to 5-deazariboflavin itself. F. Yoneda et al., J. Chem. Soc., Perkin Transactions I, 1805 (1976), disclose a process for preparing 5-deazariboflavins by cyclization of the corresponding uracil derivative with triethylorthoformate in dimethylformamide.

M. Janda and P. Hemmerich, Angew. Chem. Int. Ed. Engl., 15, 433 (1976) disclose a process for preparing 5-deazariboflavin via 6-(N-D-ribityl-3,4-xylidino)uracil wherein the ribityl side chain of said uracil derivative is acetylated prior to cyclization with POCl3 and dimethylformamide. The resulting acetylated 5-deazariboflavin is deacetylated to obtain 5-deazariboflavin.

A method for preparing 6-(N-alkylanilino)uracils is described in F. Yoneda, Y. Sakuma, M. Ichiba, and K. Shinomura, Chem. Pharm. Bull., 20, 1832 (1972); F. Yoneda and Y. Sakuma, Japanese Patent 73 99, 183 (1973); Zh. I. Litvak, S. I. Peretokina, N. I. Kirillova, and V. M. Berezovskii, Zhur, Obshch. Khim., 44, 1401 (1974) and F. Yoneda, Y. Sakuma, M. Ichiba, and K. Shinomura, J. Amer. Chem. Soc., 98, 830 (1976).

Yoneda et al. prepare 6-(N-alkylanilino)uracils by fusing 6-halogenouracils with N-alkylarylamines; sometimes in the presence of a small amount of dimethylformamide. Litvak et al. carry out the same reaction in boiling butanol solution. In some cases, especially with hydroxylated alkyl side chains, these processes have not been reproducible. The reactions do not go to completion and the products are difficult to purify.

The present invention is the process for the synthesis of 5-deazariboflavins (and alkoxymethylene and alkanoyl derivatives thereof) via a ring closure step catalyzed by a strong acid and carried out under anhydrous conditions, designed to be simple, economical and suitable for large-scale preparations. The process is set forth in general terms in Schemes (I) and (II). Scheme (IV) illustrates the process applied specifically to the preparation of 5-deazariboflavin. The key step of the process i.e., the ring closure of the uracil derivatives (III), (VIII) and (XIX) with trialkylorothoformate in the presence of a strong acid catalyst under anhydrous conditions to form 5-deazariboflavins (IV), (IX) and (XX) respectively, is illustrated by the reactions in Scheme (I), Step 2; Scheme (II), Step 3; and Scheme (IV), Step 4 respectively.

Scheme (I) and (II) differ from each other with respect to the groups present at the 8- and 10-position. The Schemes illustrate the blocking and deblocking steps necessary when reactive groups are present at these two positions. Scheme (I) illustrates the case wherein $R_{10}$ is a side chain containing hydroxy groups. Reaction of the uracil derivative (III) with a trialkylorthoformate in the presence of a strong acid catalyst selected from the group consisting of strong mineral acids, Lewis acids and organic-based acids such as sulfonic and phosphonic acids under anhydrous conditions yields an alkoxymethylene deazariboflavin (IV) which is readily hydrolyzed to give the deazariboflavin compound. Scheme (II) illustrates the case wherein reactive hydroxy groups at the 8- and 10-positions are acylated (Step 2) prior to cyclization (Step 3). After cyclization, the acyl groups are hydrolyzed (Step 4). Scheme (IV) illustrates the case wherein the specific compound 5-deazariboflavin is prepared.

An improved process for the preparation of the uracil derivatives (III), (VII) and (XIX) is also disclosed. The improvement comprises the use of an excess of the aniline derivatives (II), (VI) and (XVIII) with respect to 6-chlorouracil and the use of water as a solvent. The preferred ratio of aniline derivative to 6-chlorouracil is approximately 3:1. The advantage in using an excess of the aniline derivative is the complete reaction of the 6-chlorouracil. The excess aniline derivative is usually recoverable quantitatively at the end of the reaction.

The riboflavin derivatives wherein the side chain at the 10-position is a hydroxylated alkyl chain, such as ribityl, can be converted to the corresponding alkoxymethylene derivative. This process is illustrated by the reverse of Step 5 in Scheme (IV), wherein 5-deazariboflavin (XXI) is converted to the methoxymethylene derivative (XX) by the treatment of (XXI) with trimethylorthoformate in the presence of a sulfonic acid catalyst.

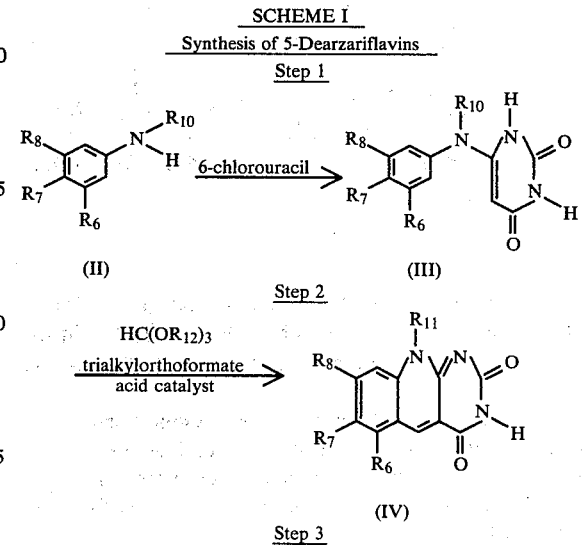

SCHEME I
Synthesis of 5-Dearzariflavins
Step 1

Step 2

Step 3

-continued
SCHEME I
Synthesis of 5-Dearzariflavins

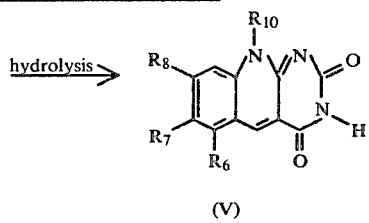

(V)

R$_6$ is H or alkyl containing 1 to 3 carbon atoms;
R$_7$ is H or methyl;
R$_8$ is alkyl containing 1 to 3 carbon atoms or hydroxy;
R$_{10}$ is —CH$_2$—(CHOH)$_m$—CH$_2$Oh
wherein m is 1 or 3; R$_{11}$ is

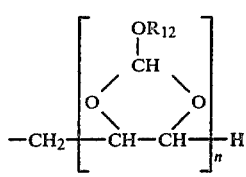

wherein R$_{12}$ is alkyl containing 1 to 2 carbon atoms and n is 1 or 2.

SCHEME II
Step 1

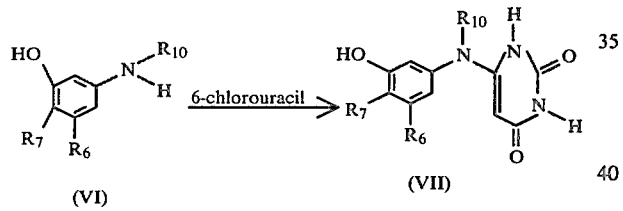

(VI)

Step 2
acylate →

(VIII)

Step 4

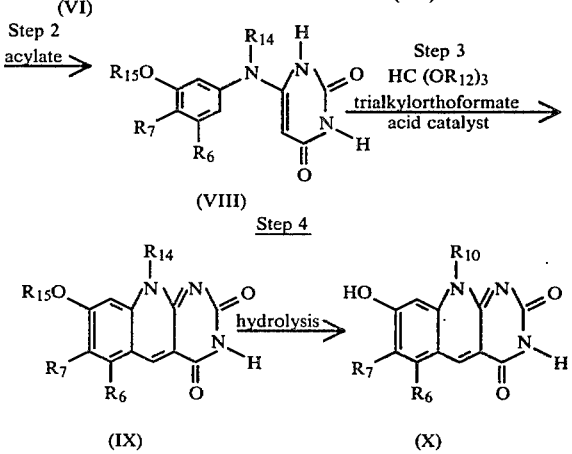

(IX)                (X)

wherein R$_6$, R$_7$, R$_{10}$ and R$_{12}$ are as defined above; R$_{14}$ is —CH$_2$—(CHOR$_{15}$)$_m$—CH$_2$OR$_{15}$ wherein R$_{15}$ is alkanoyl containing 2 to 3 carbon atoms and m is as defined above.

It is to be understood that the present process is equally applicable to the preparation of deazariboflavins having other substituents than those recited above. Illustrations of other suitable groups are set forth in Scheme III.

SCHEME III
Step 1

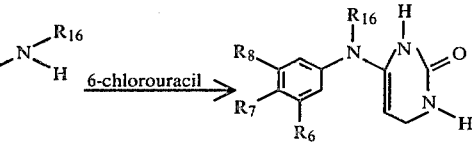

(XI)                (XII)

Step 2

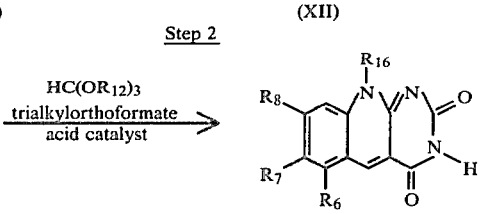

(XIII)

wherein R$_6$, R$_7$, R$_8$ and R$_{12}$ are as defined above; R$_{16}$ is

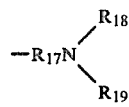

wherein R$_{17}$ is alkyl containing 2 to 4 carbon atoms; R$_{18}$ and R$_{19}$ are alkyl containing 1 to 2 carbon atoms; or a ring substituted benzyl having the structure:

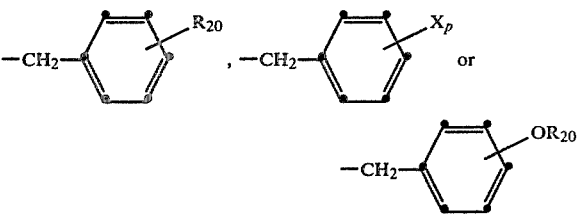

wherein R$_{20}$ is alkyl containing 1 to 3 carbon atoms; X is halogen and p is 1 to 3.

If R$_8$ is hydroxy, it may be preferred to acylate said hydroxy group prior to cyclization as illustrated in Scheme II.

The process for preparing the aniline compounds (II), (VI) and (XVIII) is known to those skilled in the art. The aniline compounds are treated in water with 6-chlorouracil wherein the molar ratio of the aniline compound to 6-chlorouracil is about 3:1. The process of the present invention is directed to cyclizing the resulting uracil derivatives (III), (VIII) and (XIX) by treating said uracil derivatives with excess trialkylorthoformate having the structure HC(OR$_{12}$)$_3$ wherein the alkyl group R$_{12}$ contains 1 to 2 carbon atoms in the presence of a strong acid catalyst under anhydrous conditions to obtain the 5-deazariboflavin compounds (IV), (IX) and (XX) and when desired hydrolyzing any blocking groups to obtain compounds (V), (X), and (XXI).

Suitable strong acid catalysts useful in carrying out the process of the present invention are strong mineral acids, Lewis acids and organic-based acids such as sulfonic and phosphonic acids. Preferred mineral acids are selected from the group consisting of anhydrous hydrochloric acid, sulfuric acid, anhydrous phosphoric acid and anhydrous phosphorus acid. Preferred Lewis acids are selected from the group consisting of $BF_3$, $ZnCl_2$, $TiCl_4$, $SnCl_4$ and $AlCl_3$. Preferred organic-based acids include sulfonic acids selected from aromatic or aliphatic sulfonic acids, such as, p-toluenesulfonic acid, benzenesulfonic acid, naphthalenesulfonic acid, methanesulfonic acid and ethanesulfonic acid and phosphonic acids such as phenylphosphonic acid.

The excess loweralkoxyorthoformate acts as both reactant and solvent. If needed, a co-solvent may be added to obtain complete solution of the uracil derivative. Suitable co-solvents are dimethylsulfoxide, acetonitrile, diglyme, tetramethylenesulfone, 1,2-dimethoxyethane and dioxane. Dimethylformamide may be employed but not in the case wherein hydroxylated side chains are present if isolation of the alkoxymethylene derivative is desired.

In the case illustrated by Scheme I wherein $R_{10}$ in compound (III) is the hydroxylated alkyl group —$CH_2$—$(CHOH)_m$—$CH_2OH$ wherein m is 1 or 3, treatment with a trialkylorthoformate results in the orthoformylation of the hydroxy groups in $R_{10}$ to give the alkoxymethylene derivative (IV) wherein $R_{11}$ has the structure:

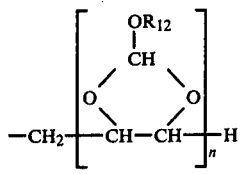

wherein $R_{12}$ is alkyl containing 1 to 2 carbon atoms and n is 1 to 2. A particular advantage of the present orthoformate cyclization is the in situ protection of the hydroxy groups in $R_{10}$ side chain by converting the hydroxy groups to stable, readily isolated alkoxymethylene derivatives which can be hydrolyzed in high yield to the desired 5-deazariboflavin derivative (V) wherein $R_{10}$ is —$CH_2$—$(CHOH)_m$—$CH_2OH$ wherein m is 1 or 3. Hydrolysis is readily carried out with dilute mineral acid such as 1N—NCl.

In the case illustrated by Scheme II, the hydroxy groups in compound (VII) are acylated prior to ring closure with trialkylorthoformate. In compound (VII), $R_{10}$ is a hydroxylated alkyl group —$CH_2$—$(CHOH)_m$—$CH_2OH$ wherein m is 1 or 3. Treatment with an acylating agent results in the acylation of the hydroxy groups in $R_{10}$ to give the corresponding acyloxy derivatives (VIII) wherein $R_{14}$ has the structure:

—$CH_2$—$(CHOR_{15})_m$—$CH_2OR_{15}$ wherein $R_{15}$ is alkanoyl containing 2 to 3 carbon atoms and m is 1 or 3. Acylation is carried out by using conventional methods, such as an acid anhydride in the presence of an organic base. Preferred acylating agents are acetic or propionic anhydride in the presence of pyridine or zinc chloride.

After cyclization of acylated (VIII) with trialkylorthoformate in the presence of a strong acid catalyst under anhydrous conditions, according to Scheme II, Step 3, the alkanoyl groups $R_{15}$ are readily removed by conventional methods, such as treatment with methanolic HCl, dilute aqueous solutions of inorganic base, such as 2.5 N NaOH or aqueous HCl solutions. The preferred method is treatment with concentrated aqueous HCl at room temperature. Removal of the alkanoyl groups provides 5-deazariboflavin derivatives (X) wherein $R_{10}$ is —$CH_2$—$(CHOH)_m$—$CH_2OH$ wherein m is 1 or 3.

The alkoxymethylene derivatives of 5-deazariboflavins having the structure:

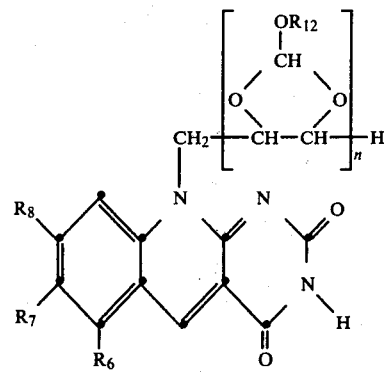

wherein $R_6$ is H or lower alkyl containing 1 to 3 carbon atoms; $R_7$ is H or methyl; $R_8$ is lower alkyl containing 1 to 3 carbon atoms; $R_{12}$ is alkyl containing 1 to 2 carbon atoms and n is 1 to 2, can also be prepared by treating the compounds having the structure:

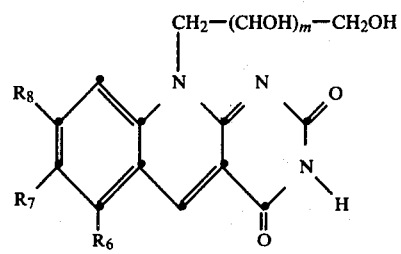

wherein $R_6$, $R_7$ and $R_8$ are as defined above and m is 1 or 3 with trialkylorthoformate wherein the alkyl group contains 1 to 2 carbon atoms in the presence of a strong acid catalyst under anhydrous conditions.

The alkoxymethylene derivatives obtained thereby are useful as prodrug forms of 5-deazariboflavin coccidiostats.

DESCRIPTION OF PREFERRED EMBODIMENTS

A preferred aspect of the present invention is the application of the process illustrated in Scheme (I) to the process for preparing 5-deazariboflavin (XXI) according to Scheme (IV). A further preferred aspect of the present invention is the application of the process illustrated in Scheme (I) to the process for preparing 7,8-didemethyl-8-hydroxy-5-deazariboflavin (according to Scheme (V).

SCHEME IV
Synthesis of 5-Deazariboflavin

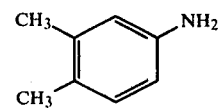

(XV)

Step 1

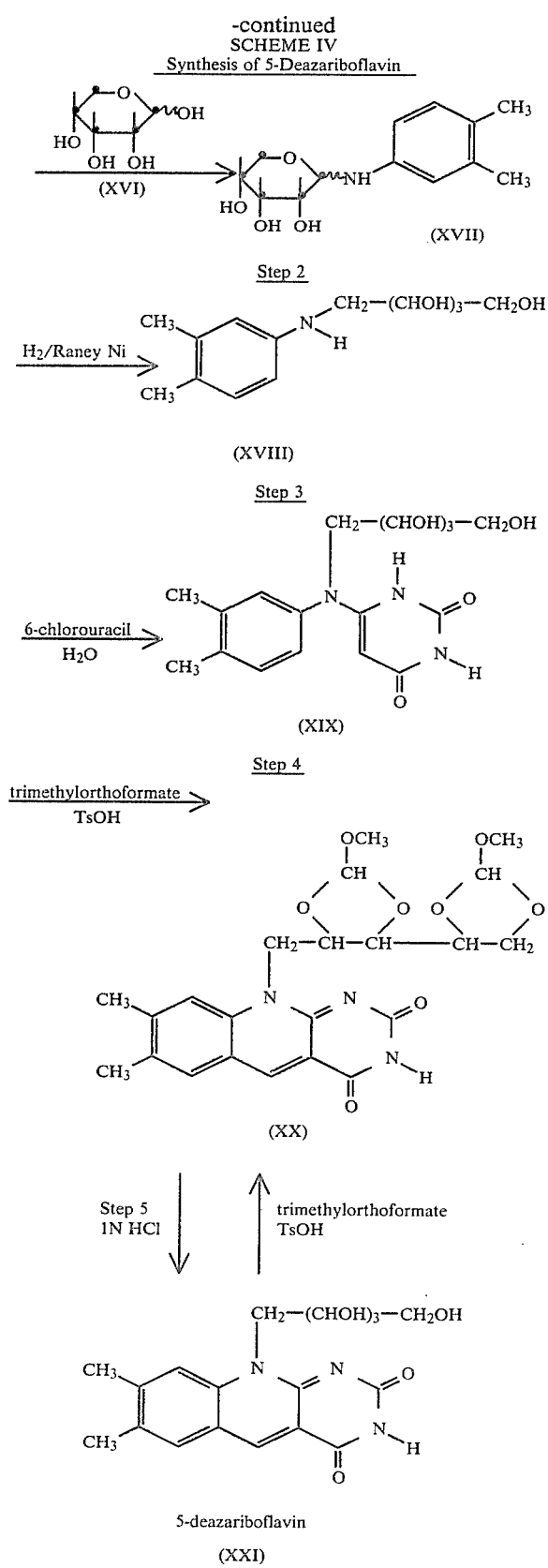

-continued
SCHEME IV
Synthesis of 5-Deazariboflavin (XVI)

Step 2
H₂/Raney Ni (XVIII)

Step 3
6-chlorouracil
H₂O (XIX)

Step 4
trimethylorthoformate
TsOH (XX)

Step 5
1N HCl trimethylorthoformate
TsOH 5-deazariboflavin
(XXI)

A preferred aspect of the present invention consists of a simple, economical synthesis, suitable for large-scale preparations, of 5-deazariboflavin (XXI) (and alkoxymethylene derivatives thereof) via the key novel step of ring closure of 6-(N-D-ribityl-3,4-xylidino)uracil (XIX) with a trialkylorthoformate according to Scheme (IV), Step 4. Reaction of (XIX) with a trialkylorthoformate in the presence of a strong acid catalyst selected from the group consisting of strong mineral acids, Lewis acids and organic-based acids such as sulfonic and phosphonic acids under anhydrous conditions yields a bis(alkoxymethylene) deazariboflavin (XX), which is readily hydrolyzed to 5-deazariboflavin (XXI).

An improved procedure for the preparation of the uracil intermediate, (XIX), comprises the use of about a 3:1 molar ratio of N-D-ribityl-3,4-xylidine (XVIII) to 6-chlorouracil and the use of water as a solvent. The use of excess N-D-ribityl-3,4-xylidine (XVIII) insures complete reaction of 6-chlorouracil. The excess (XVIII) is easily recovered at the end of the reaction. A mixture of 6-chlorouracil and about a 3× molar excess of a aniline derivative, (XVIII), is refluxed in water with stirring for a period extending from approximately 6 to 24 hours during which time virtually all the 6-chlorouracil reacts. All the reactants dissolve during the reflux period. The reaction solution is cooled and 2 equivalents (with respect to 6-chlorouracil) of inorganic base are added with stirring. The unreacted excess aniline derivative, (XVIII), is recovered, usually by simple filtration. The filtrate is acidified and evaporated to dryness in vacuo. The product is extracted from the residue into a suitable organic solvent, leaving behind inorganic salts. The solvent, containing product, is evaporated to dryness in vacuo and the residue is purified by conventional means such as recrystallization to obtain pure uracil derivative, (XIX).

A mixture of the uracil derivative, (XIX), is refluxed under an inert atmosphere with excess triloweralkylorthoformate in the presence of a strong acid catalyst under anhydrous conditions. Suitable strong acid catalysts useful in carrying out the process of the present invention are strong mineral acids, Lewis acids and organic-based acids such as sulfonic and phosphonic acids. Preferred mineral acids are selected from the group consisting of anhydrous hydrochloric acid, sulfuric acid, anhydrous phosphoric acid and anhydrous phosphorous acid. Preferred Lewis acids are selected from the group consisting of $BF_3$, $ZnCl_2$, $TiCl_4$, $SnCl_4$ and $AlCl_3$. Preferred organic-based acids include sulfonic acids selected from aromatic or aliphatic sulfonic acids, such as, p-toluenesulfonic acid, benzenesulfonic acid, naphthalenesulfonic acid, methanesulfonic acid and ethanesulfonic acid and phosphonic acids such as phenylphosphonic acid.

After a reaction time of about 6 hours to 8 days, the reaction mixture is cooled and the precipitated 5-deazariboflavin compound (XX), is collected by filtration. If the compound does not precipitate, the solvent can be removed by distillation and the crude product purified by recrystallization or chromatography. The alkoxymethylene group may be readily removed by hydrolysis to obtain 5-deazariboflavins.

The bis(alkoxymethylene) derivatives (XX) can also be prepared from (XXI) by treatment with a trialkylorthoformate in the presence of a strong acid catalyst such as p-toluenesulfonic acid under anhydrous conditions. The alkoxymethylene derivative of 5-deazariboflavin obtained thereby is useful as a prodrug form of the coccidiostat, 5-deazariboflavin.

The following Examples are given for the purpose of illustration and not by way of a limitation.

EXAMPLE 1

Preparation of 6-(N-D-Ribityl-3,4-xylidino)uracil

A 5 liter three-necked flask equipped with a mechanical stirrer and condenser was charged with a mixture of 47.0 g. (0.32 moles) of 6-chlorouracil [prepared by the process set forth in R. M. Cresswell and H. C. S. Wood, J. Chem. Soc., 4768 (1960)], 245 g. (0.96 moles) of N-D-ribityl-3,4-xylidine and 1250 ml. of water. The mixture was heated to reflux with stirring.

All the material dissolved before the onset of reflux. After 15 hours, the solution was cooled in an ice bath, resulting in heavy crystallization. Stirring was continued in the ice bath as 275 ml. (0.69 mole) of 2.5 N NaOH was added. The mixture was stirred for an additional hour in the ice bath, then filtered to recover the excess N-D-ribityl-3,4-xylidine starting material. The starting material, in the form of a tan solid, was washed with water and the washing added to the filtrate. The tan solid after drying yielded 175.4 g. of pure N-D-ribityl-3,4-xylidine.

The combined washing and filtrate were acidified to pH 3 with concentrated HCl and evaporated to dryness on the rotovac (high vac.). The residual semi-solid was extracted with 1250 ml. of boiling methanol. The insoluble solid (NaCl) was filtered off and washed with some additional hot methanol. The combined filtrate and washing were evaporated to dryness in vacuo. The residual gum was dissolved in 300 ml. hot $H_2O$. On cooling and seeding, crystallization began. After standing 48 hours, the solid was collected by filtration and washed with cold $H_2O$ and acetone. Yield of cream-colored crystals: 70.1 g. (57% calculated for the monohydrate), m.p. 183°–185° C. (slight preliminary softening) [literature m.p. 185° C., F. Yoneda, et al., J. Am. Chem. Soc., 98, 830 (1976)]. Tlc in (80:20:2 $CHCl_3$—MeOH—$H_2O$) showed essentially a single spot.

EXAMPLE 2

Preparation of 2′,3′,4′,5′-Bis-O-methoxymethylene-5-deazariboflavin

A mixture of 3.65 g. (10 mmoles) of 6-(N-D-ribityl-3,4-xylidino)uracil, 30 ml. of trimethylorthoformate, and 200 mg. of p-toluenesulfonic acid monohydrate was refluxed with stirring under nitrogen. After 4 days, considerable crystallization had occurred, and the mixture was cooled. The solid was collected by filtration and washed with acetone. Yield of fine yellow crystals: 2.06 g. (45%), m.p. 276°–278° C. (dec., preliminary softening). Tlc in (9:1 $CHCl_3$—MeOH) showed essentially a single spot with charring.

Calculated for $C_{22}H_{25}N_3O_8$: C, 57.51; H, 5.48; N, 9.15; Found: C, 56.98; H, 5.36; N, 9.02.

EXAMPLE 3

Preparation of 5-Deazariboflavin

A suspension of 23.4 g. (51 mmoles) of 2′,3′,4′,5′-bis-O-methoxymethylene-5-deazariboflavin in 500 ml. of 1 N HCl was heated on a steam bath with intermittent stirring. Complete solution was never obtained because crystallization of product began before all the starting material dissolved. After 45 minutes, by which time tlc showed complete reaction, the mixture was cooled and neutralized with excess saturated $NaHCO_3$. The product was collected by filtration and washed with $H_2O$, then with acetone. Yield of fluffy yellow crystals: 19.37 g. (97% calculated for the monohydrate) m.p. 289°–292° C. (dec. preliminary softening). [Lit. m.p. 286°–288° C. dec. reported in D. E. O'Brien, L. T. Weinstock, and C. C. Cheng, Chem. and Ind., 2044 (1967) and D. E. O'Brien, L. T. Weinstock and C. C. Cheng, J. Heterocycl. Chem., 7, 99 (1970)]. Tlc in (80:20:2 $CHCl_3$—MeOH—$H_2O$) showed a single spot (bright blue fluorescence with yellow core).

Calculated for $C_{18}H_{21}N_3O_6 \cdot H_2O$: C, 54.95; H, 5.89; N, 10.68 Found: C, 55.22; H, 5.78; N, 10.59.

EXAMPLE 4

Preparation of 5-(1-D-Ribosylamino)-o-cresol

A solution of 17.2 g. (140 mmole) of 5-amino-o-cresol and 21.0 g. (140 mmole) of D-ribose in 180 ml. of methanol was refluxed with stirring protected from moisture with a drying tube. After 2 hours, the solution was cooled. Tlc in (80:20:2 $CHCl_3$—MeOH—$H_2O$) indicated nearly complete reaction. The solution was used directly in Example 5 without isolating the product.

EXAMPLE 5

Preparation of 5-D-Ribitylamino-o-cresol

To a solution of crude 5-D-ribosylamino-o-cresol (140 mmole) in 180 ml. of methanol, prepared by the process set forth in Example 4, was added Raney nickel (14.0 g.) and the mixture was hydrogenated at 600 psi and 70° C. for 7 hours. Tlc in (80:80:2 $CHCl_3$—MeOH—$H_2O$) showed that the reaction was essentially complete. The catalyst was removed by filtration, and the filtrate was concentrated on the rotovac to give 39.0 g. (108%) of viscous, yellow-brown oil. The oil solidified after standing for several days. The light brown, amorphous solid had a m.p. of 107°–115° C. with preliminary softening.

EXAMPLE 6

Preparation of 6-[3-Acetoxy-4-methyl-N-(2′,3′,4′,5′-tetra-O-acetyl-1-D-ribityl)anilino]uracil A solution of 3.0 g. 6-chlorouracil and 16.8 g. (3× molar excess) 5-D-ribitylamino-o-creson in 80 ml. water was refluxed for 7 hours. Tlc in (80:20:2 $CHCl_3$—MeOH—$H_2O$) showed only excess 5-D-ribitylamino-o-cresol and product. The water was evaporated under vacuum. The residue was slurried with ethanol and concentrated to a viscous syrup.

The crude product was acetylated in 40 ml. acetic anhydride and 100 ml. pyridine with ice-bath cooling under a nitrogen atomosphere for 16 hours. The crude product was concentrated to a small volume and diluted with chloroform. The chloroform solution was washed with water 3×, cold dilute HCl 1× and dried with anhydrous $Na_2SO_4$. The dry solution was concentrated, in vacuo, to yield 23 g. of a crude viscous oil.

The crude viscous oil was applied to a 60 cm × 8 cm column packed with silica gel in methylene chloride and eluted with 3 l. methylene chloride; 3 l. methylene chloride-methanol 200:1; 3 l. methylene chloride-methanol 100:1; and finally 3 l. methylene chloride-methanol 50:1. Fractions of 25 ml. were collected.

The product appeared in fractions 230 to 350. These fractions were pooled and the solvent evaporated in vacuo to give 6.1 g. of product.

EXAMPLE 7

Preparation of
8-Demethyl-8-hydroxy-5-deazariboflavin-2',3',4',5',8-penta-O-acetate A solution of 6-[3-acetoxy-4-methyl-N-(2',3',4',5'-tetra-O-acetyl-1-D-ribityl)anilino]uracil, 5.6 g., prepared by the process of Example 6, in 50 ml. triethylorthoformate and 12 ml. dimethylsulfoxide (DMSO) containing 220 mg. p-toluenesulfonic acid monohydrate was heated for 16 hours at 95° C. and 8 hours at 115° C.

The reaction solution was concentrated in vacuo to a small volume, diluted with chloroform and washed with water 2×. The chloroform solution was dried with anhydrous $Na_2SO_4$ and the solvent evaporated in vacuo to give 4.7 g. of crude product.

The crude product was applied on a 7 cm. diameter column packed with 500 g. silica gel in methylene chloride. The column was eluted with 3 l. portions of the following solvents and 25 ml. fractions were collected:
(1) methylene chloride
(2) methylene chloride-methanol 200:1
(3) methylene chloride-methanol 100:1
methylene chloride-methanol 200:3
(5) methylene chloride-methanol 50:1

The crude product appeared in fractions 90 to 160. These fractions were pooled and the solvent evaporated to yield 1.4 g. of crude product. The crude product was recrystallized from ethanol to give 0.52 g. of a yellow solid m.p. 180°-184° C. A small portion was further recrystallized from methanol to give yellow crystals m.p. 187°-189° C. (preliminary softening).

Calculated for $C_{27}H_{29}N_3O_{12}$: C, 55.19; H, 4.98; N, 7.15.

Calculated for $C_{27}H_{29}N_3O_{12} \cdot \frac{3}{4} H_2O$: C, 53.95; H, 5.11; N, 6.99; Found C, 53.89; H, 5.15; N, 7.02.

EXAMPLE 8

Preparation of
8-Demethyl-8-hydroxy-5-deazariboflavin

A solution of 235 mg (0.4 mmole) of 8-demethyl-8-hydroxy-5-deazariboflavin-2',3',4',5',8-penta-O-acetate in 4 ml. of concentrated HCl was allowed to stand at room temperature. After 23 hours, the solution was filtered and diluted gradually with $H_2O$ until crystallization began. After standing, the solid product was collected on a filter and washed thoroughly with $H_2O$, then methanol and finally acetone. Yield of yellow solid: 50 mg., m.p. 311°-313° C. (dec. with preliminary softening). A second crop was obtained from the $MeOH-Me_2CO$ filtrate: 30 mg. of yellow solid, m.p. 313°-314° C. (preliminary softening). Similarly obtained was a third crop, 20 mg., m.p. 307°-308° C. (preliminary softening). Total yield = 100 mg. (66% yield).

Calculated for $C_{17}H_{19}N_3O_7 \cdot \frac{1}{2} H_2O$: C, 52.85; H, 5.22; N, 10.88; Found: C, 53.05; H, 5.36; N, 10.75.

EXAMPLE 9

Preparation of
2',3',4',5'-Bis-O-methoxymethylene-5-deazariboflavin

A suspension of 196 mg. (0.50 mmole) of 5-deazariboflavin and 15 mg. of p-toluenesulfonic acid monohydrate in 5 ml. of trimethylorthoformate was stirred under reflux. DMSO (2.2 ml. total) was added gradually at the boiling point until all the solid had dissolved. After 5 minutes, tlc in (9:1 $CHCl_3$—MeOH) had indicated complete conversion to product. The solution was cooled and diluted to 100 ml. with methanol. Crystallization began rapidly after dilution with methanol. After further cooling and stirring, the product was isolated by filtration and washed with methanol and with ether. Yield of yellow solid = 103 mg., m.p. 277°-279° C. (dec. preliminary softening). A second crop (20 mg.) had m.p. 275°-277° C. (dec. preliminary softening). Tlc in (9:1 $CHCl_3$—MeOH) showed a single spot. Total yield = 123 mg. (54%).

EXAMPLE 10

Preparation of
2',3',4',5'-Bis-O-ethoxymethylene-5-deazariboflavin

A suspension of 196 mg. (0.50 mmole) of 5-deazariboflavin and 15 mg. of p-toluenesulfonic acid monohydrate in 5 ml. of triethylorthoformate was stirred at 100°-110° C. as 0.7 ml. of DMSO was added. All the solid dissolved. Tlc in (9:1 $CHCl_3$—MeOH) immediately after dissolution indicated complete reaction. After 5 minutes, at 110°-115° C., the solution was cooled, resulting in crystallization of product. After dilution with ethanol the solid was collected on a filter and washed with ethanol and with ether. Yield of yellow crystals = 130 mg. (51%), m.p. 230°-233° C., (dec.) Tlc (9:1 $CHCl_3$—MeOH) showed a single spot.

SCHEME V
Synthesis of 7,8-Didemethyl-8-hydroxy-5-deazariboflavin

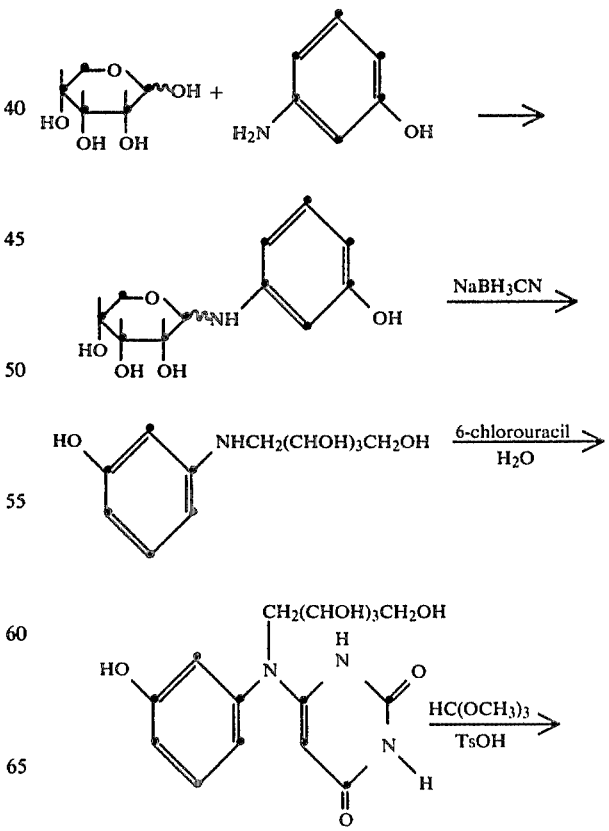

13
-continued
SCHEME V
Synthesis of 7,8-Didemethyl-8-hydroxy-5-deazariboflavin

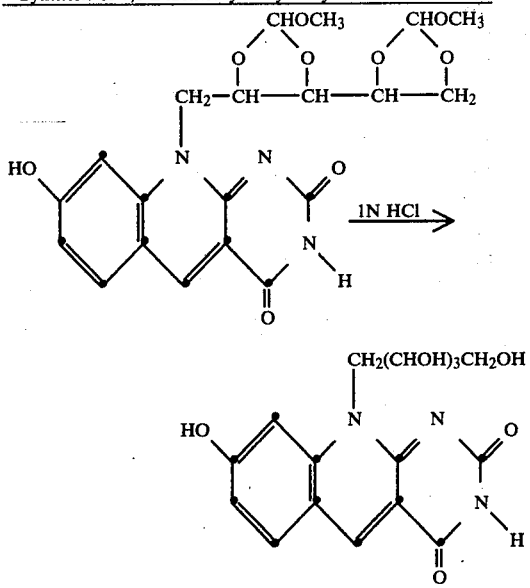

This synthetic route is the same as that used to prepare 5-deazariboflavin, Scheme IV, with the exception that the N-ribosyl intermediate was reduced to the corresponding N-ribityl by sodium cyanoborohydride rather than by catalytic hydrogenation. In this case, substantial reduction of the aromatic ring occurred under hydrogenation conditions.

EXAMPLE 11

Preparation of 3-(1-D-Ribosylamino)phenol

A mixture of 37.5 g. (0.25 mole) of D-ribose, 27.25 g. (0.25 mole) of m-aminophenol, and 150 ml. of methanol was refluxed with stirring under nitrogen for 4 hours. The resulting solution was concentrated to a small volume and diluted with 20 ml. of isopropanol. The product which crystallized was collected on a filter and washed with small quantities of isopropanol, then with ether, giving 48 g. (79%) of off-white crystals, m.p. 144° C. dec. (from cold methanol). Tlc (80:20:2, CHCl$_3$—MeOH—H$_2$O) showed one major spot. The material was unstable and preferably was used directly in the next step.

EXAMPLE 12

Preparation of 3-D-Ribitylaminophenol

A mixture of 96 g. (0.4 mole) of 3-(1-D-ribosylamino)phenol, 5 ml. of acetic acid, and 1500 ml. of dry methanol was stirred under nitrogen in an ice bath at 10° C. as 40 g. (0.64 mole) of sodium cyanoborohydride was added in small portions. The reaction mixture was then stirred at room temperature for 16 hours. The pH was adjusted to 2 with concentrated HCl. (Caution: evolution of HCN and H$_2$.) After gas evolution has subsided, the pH was readjusted to 4 by addition of solid lithium hydroxide in small portions. This solution was stirred with 300 ml. of AG50-X8 cation-exchange resin (100–200 mesh) until renewed effervescence subsided. This entire mixture was packed on top of a bed of 300 ml. of additional prewashed resin in a column (8 cm. diameter). The column was washed with 4 l. of H$_2$O. The product was then eluted with 1% NH$_4$OH solution. Fractions containing the desired material were combined and concentrated in vacuo at 40° C. The residue was redissolved in methanol and treated with charcoal. The filtered solution was evaporated to give a solid, which was washed with acetone. Total yield of light gray solid was 78 g. (80%). Tlc (80:20:2, CHCl$_3$—MeOH—H$_2$O) showed essentially a single spot. The analytical sample purified by high pressure liquid chromatography had m.p. 133°–135° C. (dec.)

Calculated for C$_{11}$H$_{17}$NO$_5$: Calc.: C, 54.31; H, 7.05; N, 5.76; Found: C, 54.46; H, 6.90; N, 5.84.

EXAMPLE 13

Preparation of 6-(3-Hydroxy-N-D-ribitylanilino)uracil

A solution of 33 g. (136 mmoles) of 3-D-ribitylaminophenol and 6.4 g. (43.5 mmoles) of 6-chlorouracil in 50 ml. of water was stirred at reflux under nitrogen for 14 hours. The solution was then added to a column containing 300 ml. of prewashed AG50-X8 cation-exchange resin. After elution with 3 l. of H$_2$O, fractions containing product were combined and concentrated under nitrogen to yield 7.1 g. of glassy residue (46% based on 6-chlorouracil; 70% based on recovered 3-D-ribitylaminophenol, which subsequently was eluted from the column with 1% NH$_4$OH). The material was suitable for use in the next step.

EXAMPLE 14

Preparation of 2',3',4',5'-Bis-O-methoxymethylene-7,8-didemethyl-8-hydroxy-5-deazariboflavin A mixture of 2.00 g. (5.67 mmoles) of 6-(3-hydroxy-N-D-ribitylanilino)uracil, 0.14 g. of p-toluenesulfonic acid monohydrate, and 60 ml. of trimethyl orthoformate was stirred at reflux under nitrogen. Precipitation of product began within a few minutes. After 18 hours, the mixture was cooled. The solid was collected on a filter and washed with small volumes of methanol until the washings were only light yellow. Yield of golden-yellow solid was 1.05 g. (41%), m.p.>251° C. (dec.).

Calculated for C$_{20}$H$_{21}$N$_3$O$_9$: Calc.: C, 53.69; H, 4.73; N, 9.39; Found: C, 53.29; H, 4.68; N, 9.17.

EXAMPLE 15

Preparation of 7,8-Didemethyl-8-hydroxy-5-deazariboflavin

A suspension of 894 mg. (2.00 mmoles) of 2',3',4',5'-bis-O-methoxymethylene-7,8-didemethyl-8-hydroxy-5-deazariboflavin in 1 N HCl was heated on a steam bath, resulting in fairly rapid dissolution. After heating for an additional 30 minutes, the hot solution was filtered. The filtrate was diluted to 100 ml. with H$_2$O. The mixture was reheated to dissolve the precipitated solid and then allowed to cool slowly. After standing, the crystallized product was isolated by filtration and washed with H$_2$O and then with acetone. After drying under high vacuum at 100° C., there was obtained 611 mg. (83%) of golden-yellow crystals, m.p. 284°–286° C. (dec.). The material was homogeneous by tlc (70:30:3, CHCl$_3$—MeOH—H$_2$O).

Calculated for C$_{16}$H$_{17}$N$_3$O$_7$·½H$_2$O: Calc.: C, 52.24; H, 4.80; N, 11.42; Found: C, 52.35; H, 4.81; N, 11.35.

Any departure from the above description which conforms to the present invention is intended to be included within the scope of the claims.

What is claimed is:

1. The process for preparing di-O-alkoxymethylene-5-deazariboflavins having the structure:

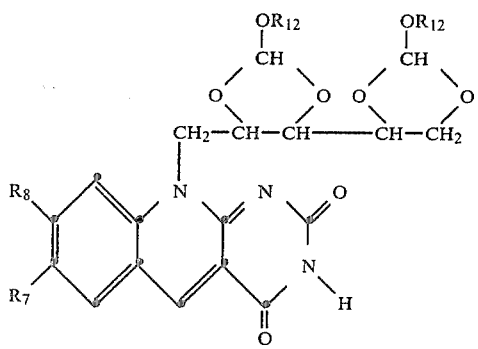

wherein $R_7$ is H or methyl; $R_8$ is alkyl having 1 to 3 carbon atoms or hydroxy; $R_{12}$ is alkyl having 1 to 2 carbon atoms which comprises cyclizing the uracil derivatives having the structure:

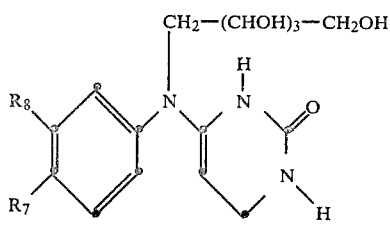

wherein $R_7$ and $R_8$ are as defined above, by treating said uracil derivatives with trialkylorthoformate having the structure:

$HC(OR_{12})_3$ wherein $R_{12}$ is as defined above in the presence of a strong acid catalyst selected from the group consisting of strong mineral acids, selected from anhydrous hydrochloric acid, sulfuric acid, anhydrous phosphoric acid and anhydrous phosphorous acid, Lewis acids and organic-based acids selected from the group consisting of sulfonic acids selected from p-toluenesulfonic acid, benzenesulfonic acid, naphthalene sulfonic acid methane sulfonic acid and ethane sulfonic acid, and phosphonic acids selected from phenyl phosphonic acid, under anhydrous conditions.

2. The process according to claim 1 wherein $R_7$ and $R_8$ are methyl.

3. The process according to claim 1 wherein $R_7$ is hydrogen and $R_8$ is hydroxy.

4. The process according to claim 1 wherein $R_7$ is methyl and $R_8$ is hydroxy.

5. The process according to claim 1 wherein said bis-O-alkoxymethylene-5-deazariboflavins are hydrolyzed.

6. The process according to claim 2 wherein said bis-O-alkoxymethylene-5-deazariboflavin is hydrolyzed to obtain 5-deazariboflavin.

7. The process according to claim 3 wherein said bis-O-alkoxymethylene-5-deazariboflavin is hydrolyzed to obtain 7,8-didemethyl-8-hydroxy-5-deazariboflavin.

8. The process according to claim 4 wherein said bis-O-alkoxymethylene-5-deazariboflavin is hydrolyzed to obtain 8-demethyl-8-hydroxy-5-deazariboflavin.

9. The process according to claim 5 wherein said hydrolysis is carried out in dilute mineral acid.

10. The process according to claim 1 wherein the strong mineral acids are selected from the group consisting of anhydrous hydrochloric acid, sulfuric acid, anhydrous phosphoric acid and anhydrous phosphorous acid.

11. The process according to claim 1 wherein the Lewis acids are selected from the group consisting of $BF_3$, $ZnCl_2$, $TiCl_4$, $SnCl_4$ and $AlCl_3$.

12. The process according to claim 1 wherein the organic-based acids are selected from the group of sulfonic acids consisting of p-toluenesulfonic acid, benzenesulfonic acid, naphthalenesulfonic acid, methanesulfonic acid and ethanesulfonic acid and the phosphonic acid, phenylphosphonic acid.

13. The process for preparing 8-demethyl-8-hydroxy-5-deazariboflavin-2',3',4',5',8-penta-O-alkanoates having the structure:

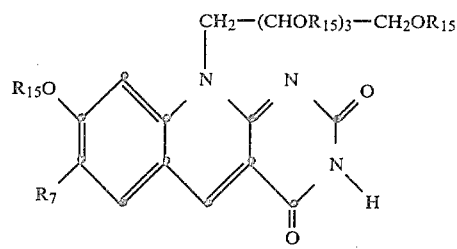

wherein $R_7$ is H or methyl; $R_{15}$ is alkanoyl containing 2 to 3 carbon atoms which comprises cyclizing the uracil derivative having the structure:

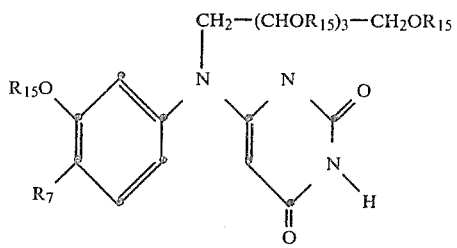

wherein $R_7$ and $R_{15}$ are as defined above by treating said uracil derivative with trialkylorthoformate having the structure:

$HC(OR_{12})_3$ wherein $R_{12}$ is alkyl containing 1 to 2 carbon atoms in the presence of a strong acid catalyst selected from the group consisting of strong mineral acids, Lewis acids and organic-based acids selected from the group consisting of sulfonic and phosphonic acids under anhydrous conditions.

14. The process according to claim 13 wherein $R_7$ is methyl and wherein said 8-demethyl-8hydroxy-5-deazariboflavin-2',3',4',5',8-penta-O-alkanoate is hydrolyzed to obtain 8-demethyl-8-hydroxy-5-deazariboflavin.

15. The process according to claim 13 wherein $R_7$ is H and wherein said 8-demethyl-8-hydroxy-5-deazariboflavin-2',3',4',5',8-penta-O-alkanoate is hydrolyzed to 7,8-didemethyl-8-hydroxy-5-deazariboflavin.

16. The process according to claim 14 wherein said hydrolysis is carried out in methanolic or aqueous HCl or dilute sodium hydroxide solution.

17. The process according to claim 15 wherein said hydrolysis is carried out in methanolic or aqueous HCl or dilute sodium hydroxide solution.

18. The process according to claim 13 wherein the strong mineral acids are selected from the group consisting of anhydrous hydrochloric acid, sulfuric acid, anhydrous phosphoric acid and anhydrous phosphorous acid.

19. The process according to claim 13 wherein the Lewis acids are selected from the group consisting of $BF_3$, $ZnCl_2$, $TiCl_4$, $SnCl_4$ and $AlCl_3$.

20. The process according to claim 13 wherein the organic-based acids are selected from the group of sulfonic and phosphonic acids consisting of p-toluenesulfonic acid, benzenesulfonic acid, naphthalenesulfonic acid, methanesulfonic acid and ethanesulfonic acid and the phosphonic acid, phenylphosphonic acid.

* * * * *

UNITED STATES PATENT AND TRADEMARK OFFICE
CERTIFICATE OF CORRECTION

PATENT NO. : 4,277,603
DATED : July 7, 1981
INVENTOR(S) : RICHARD L. TOLMAN et al It is certified that error appears in the above-identified patent and that said Letters Patent are hereby corrected as shown below:

On the title page in the abstract line 9 bracket should be reverse "anilino[..." should read "anilino]..."

Column 2 line 8 "Scheme" should be "Schemes "

Column 3 line 17 "$CH_2Oh$" should read "$CH_2OH$"

Column 4 structure (XII) 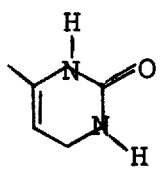 should be 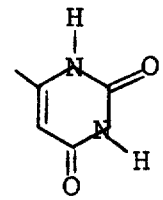

Column 5 line 43 "1N-NCl" should read "1N-HCl"

Column 15 second structure 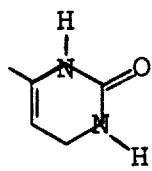 should be 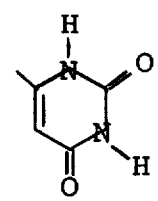

UNITED STATES PATENT AND TRADEMARK OFFICE
CERTIFICATE OF CORRECTION

PATENT NO. : 4,277,603                    Page 2 of 2
DATED       : July 7, 1981
INVENTOR(S) : Richard L. Tolman et al.

It is certified that error appears in the above—identified patent and that said Letters Patent is hereby corrected as shown below:

Column 16, line 61, "18-demethyl-8hydroxy-5-...." should read

-- 8-demethyl-8-hydroxy-5-....

*Signed and Sealed this*

*Second* Day of *February 1982*

[SEAL]

*Attest:*

*Attesting Officer*

GERALD J. MOSSINGHOFF
*Commissioner of Patents and Trademarks*